(12) United States Patent
Rösch et al.

(10) Patent No.: US 8,197,415 B2
(45) Date of Patent: Jun. 12, 2012

(54) NON-INVASIVE HEART MONITORING APPARATUS AND METHOD

(75) Inventors: Norbert Rösch, Trier (DE); Patrick Harpes, Hollenfels (LU); Daniel Wagner, Bertrange (LU); Pierre Plumer, Luxembourg (LU)

(73) Assignee: Centre de Recherche Public Henri Tudor (LU)

( * ) Notice: Subject to any disclaimer, the term of this patent is extended or adjusted under 35 U.S.C. 154(b) by 1403 days.

(21) Appl. No.: 11/573,156

(22) PCT Filed: Jul. 19, 2005

(86) PCT No.: PCT/EP2005/053469
§ 371 (c)(1),
(2), (4) Date: Feb. 2, 2007

(87) PCT Pub. No.: WO2006/013154
PCT Pub. Date: Feb. 9, 2006

(65) Prior Publication Data
US 2007/0225609 A1    Sep. 27, 2007

(30) Foreign Application Priority Data
Aug. 5, 2004  (EP) .................................. 04103780

(51) Int. Cl.
*A61B 5/02* (2006.01)
(52) U.S. Cl. ........................................ 600/485; 600/500
(58) Field of Classification Search .................... 600/481
See application file for complete search history.

(56) References Cited

U.S. PATENT DOCUMENTS

| | | |
|---|---|---|
| 2001/0012916 A1 | 8/2001 | Deuter |
| 2002/0055672 A1 | 5/2002 | Zhang |
| 2002/0193692 A1 | 12/2002 | Inukai et al. |

FOREIGN PATENT DOCUMENTS

EP    0 445 809    9/1991

OTHER PUBLICATIONS

Pulse Wave Velocity as a Measure of Blood Pressure Change Brian Gribbin, Andrew Steptoe, Peter Sleight Psychophysiology vol. 13, Issue 1, pp. 86-90, Jan. 1976.*

(Continued)

*Primary Examiner* — Charles A Marmor, II
*Assistant Examiner* — Karen Toth
(74) *Attorney, Agent, or Firm* — Woodard, Emhardt, Moriarty, McNett & Henry LLP

(57) ABSTRACT

The present invention discloses an apparatus for non-invasive heart monitoring comprising a pulse wave transit time (PWTT) determining device for determining a PWTT at predefined intervals, a first storing means for storing PWTT values resulting of the determining, a blood pressure measuring device for measuring a blood pressure close in time with the determining and a second storing means for storing blood pressure values resulting of the measuring. Furthermore, the apparatus comprises a cardiovascular dynamic change calculating device for calculating a relative change of the PWTT values and the blood pressure values as a function of time. The apparatus further comprises an alarm emitting device for emitting an alarm if the blood pressure values are substantially constant as a function of time and the PWTT values decrease as a function of time. A method for non-invasive heart monitoring is also disclosed.

17 Claims, 6 Drawing Sheets

OTHER PUBLICATIONS

Figure 1:
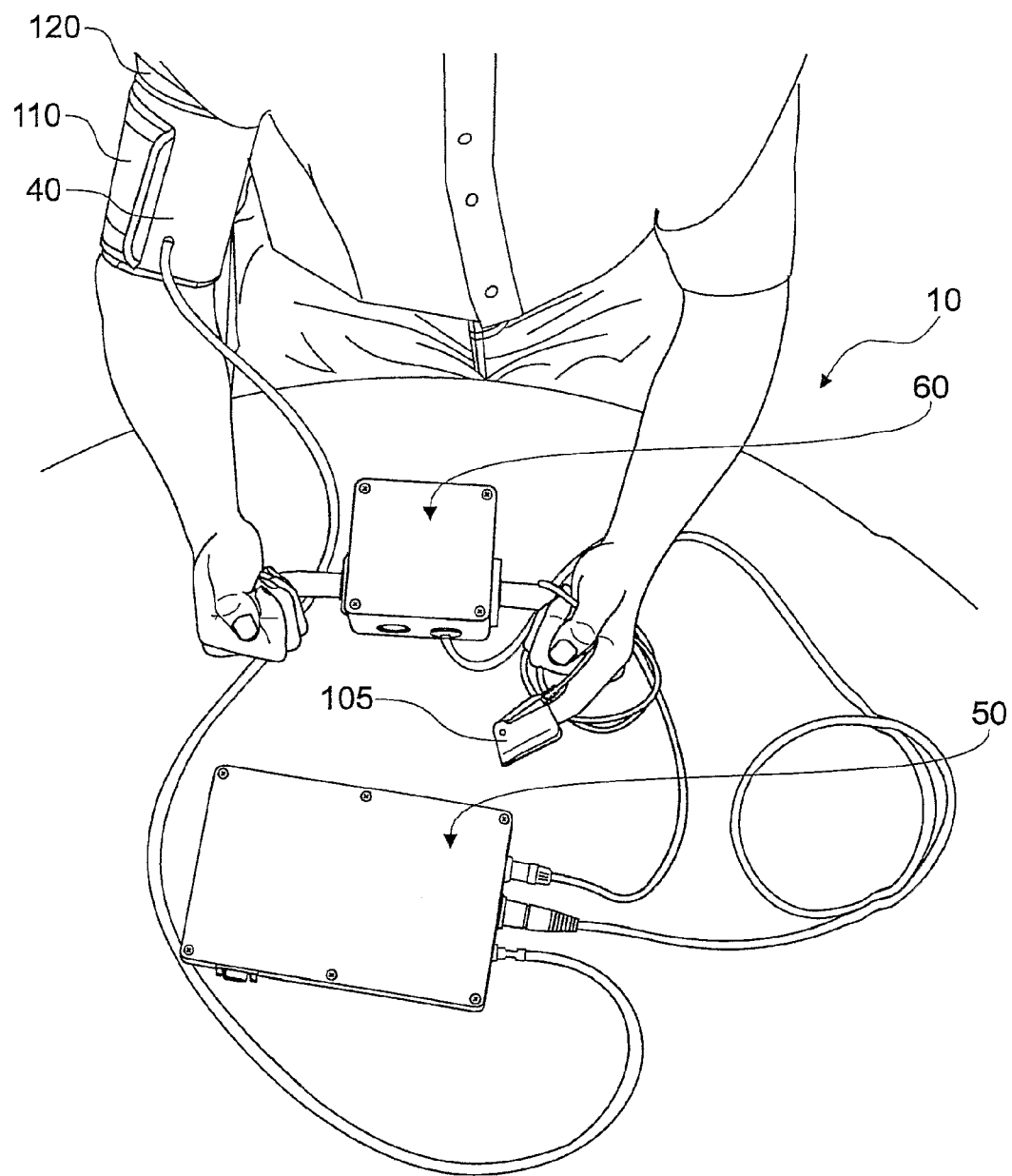

Cuff-less and Noninvasive Measurements of Arterial Blood Pressure by Pulse Transit Time C.C.Y. Poon and Y.T. Zhang Proceedings of the 2005 IEEE Engineering in Medicine and Biology 27th Annual Conference Shanghai, China, Sep. 1-4, 2005.*

Continuous Blood Pressure Monitoring using Pulse Wave Transit Time Gu-Young Jeong, Kee-Ho Yu and Nam-Gyun Kim ICCAS2005 Jun. 2-5, Kintex, Gyeonggi-Do, Korea.*

Continuous estimation of systolic blood pressure using the pulse arrival time and intermittent calibration W. Chen T. Kobayashi S. Ichikawa Y. Takeuchi T. Togawa Medical & Biological Engineering & Computing 2000, vol. 38.*

Continuous Noninvasive Blood Pressure Measurement by Pulse Transit Time Parry Fung, Guy Dumont, Craig Ries, Chris Mott, Mark Ansermino Proceedings of the 26th Annual International Conference of the IEEE EMBS San Francisco, CA, USA • Sep. 1-5, 2004.*

Continuous blood pressure monitoring during exercise using pulse wave transit time measurement J. Lass, K.Meigas, D. Karai, R. Kattai, J. Kaik, M. Rossmann Proceedings of the 26th Annual International Conference of the IEEE EMBS San Francisco, CA, USA • Sep. 1-5, 2004.*

* cited by examiner

NON-INVASIVE HEART MONITORING APPARATUS AND METHOD

This application is a National Stage filing of International Application PCT/EP2005/053469, filed Jul. 19, 2005, claiming priority to European Application No. EP 04 103 780.5, filed Aug. 5, 2004. The subject application claims priority to PCT/EP2005/053469 and to European Application No. EP 04 103 780.5 and both references are expressly incorporated by reference herein, in their entirety.

INTRODUCTION

The present invention relates to an apparatus and a method for non-invasive heart monitoring.

Cardiovascular dynamic changes of subjects are important to be monitored with a high accuracy and without giving load on the subject. Especially, subjects with a cardiovascular disease need to be frequently monitored. Due to the complex design and high costs of conventional cardiovascular monitoring apparatuses, monitoring is generally restricted to medical facilities such as hospitals.

The number of hospital admissions can be reduced in many cases through efficient home monitoring of a patient. In particular, patients with severe congestive heart failure (CHF) have frequent hospital admissions with intensive and long hospital stays. Therefore, CHF has become a major health care problem, and health care costs related to CHF are increasing dramatically. The frequent hospital admissions are due to the nature of this cardiovascular disease and to the fact that the deterioration of the condition is often insidious and can often only be recognized by the patient or his physician when it is too late for out-patient therapy.

It is believed that home monitoring will improve the surveillance of the patient and help identify significant changes in the patient's condition in time to prevent unnecessary hospital admissions. In order to recognize individual trends in the patient's condition, it is essential to measure important physiological parameters with a monitoring apparatus and to apply a well-defined monitoring method in order to evaluate the measured parameters and to draw a safe and accurate medical conclusion.

The acquisition of parameters to be monitored should not overburden the patient because this could lead to rejection and measuring errors. A simple handling of the apparatus is thus of decisive importance for establishing a home monitoring system. The attending physician and nursing staff will follow the variation of the physiological parameters of their CHF patients and intervene, when necessary. Such a home monitoring system will have a significant effect on the quality of life and the health care costs of patients with severe CHF.

OBJECT OF THE INVENTION

The object of the present invention is to provide an improved apparatus and method for non-invasive monitoring of cardiovascular changes. This object is achieved by an apparatus as claimed in claim 1 and a method as claimed in claim 7.

General Description of the Invention

In order to overcome the abovementioned problems, the present invention proposes an apparatus for non-invasive heart monitoring comprising a pulse wave transit time (PWTT) determining device for determining a PWTT at predefined intervals, a first storing means for storing resulting PWTT values, a blood pressure measuring device for measuring a blood pressure close in time with the determining and a second storing means for storing resulting blood pressure values.

It is an important aspect of the present invention that the apparatus further comprises a cardiovascular dynamic change calculating device for calculating a relative change of the PWTT values and the blood pressure values as a function of time. According to the invention, the apparatus further comprises an alarm emitting device for emitting an alarm if the blood pressure values are substantially constant as a function of time and the PWTT values decrease as a function of time.

The PWTT is defined as the time period required for a pulse wave to travel from one arterial point to another point, where the pulse could be detected. It will be appreciated that the passage of such a pulse wave through an arterial point may be measured by a pulse wave measuring device.

Preferably, one of these arterial points is chosen to be the heart such that the time of start of a pulse wave can be measured by a heart rhythm measuring system. Advantageously, such a heart rhythm measuring system comprises an electrocardiogram measuring device and a QRS-wave detecting device for detecting a QRS-wave on the electrocardiogram. It will further be appreciated that the heart rhythm measuring system may also be realized in form of an impedance plethysmograph or a phonocardiograph.

It is advantageous that the apparatus can be connected to a host system. The processed data i.e. the relative change of the PWTT values and the blood pressure values as a function of time will thus be transmitted to the host system.

In an alternative embodiment, the raw data i.e. input data to be used for the PWTT determination and the measured outputs from the blood pressure measuring device are transmitted to the host system. The PWTT determining device can then be integrated in the host system, and the determination of the PWTT can be done in the host system itself. In this way, the costs of a single home monitoring apparatus can be reduced. The input data to be used for the PWTT determination are e.g. measured outputs from the heart rhythm measuring system and the pulse wave measuring device.

Finally, also the cardiovascular dynamic change device and the alarm emitting device can be included in the host system. As the PWTT determining device, the cardiovascular dynamic change calculating device and the alarm emitting device are centralized in the host system the costs for remotely monitoring the patient are reduced.

Preferably, the list of physiological parameters to be observed is extended. For instance for patients with congestive heart failure it is advantageous to monitor also the human weight. Other interesting parameters are for example the heart rate variability, the breathing frequency, the blood sugar level, the oxygen saturation of the blood and the pulmonary function of the patient. Devices measuring these parameters will then be added to the apparatus.

It remains to be noted that the pulse wave measuring device is preferentially a photoplethysmograph based on a SpO2 measuring device. The SpO2 measuring device could also be used for a measurement of the blood oxygen saturation by determining the percentage of oxihemoglobin in a given body part (e.g. finger tip).

The present invention also discloses a method for non-invasive heart monitoring comprising the steps of:
- determining a PWTT at predefined intervals;
- storing PWTT values resulting of the determining;
- measuring a blood pressure close in time with the determining of the PWTT;
- storing blood pressure values resulting of the measuring.

According to the invention, the method further comprises the steps of:
- calculating a relative change of the PWTT values and the blood pressure values as a function of time;
- emitting an alarm if the blood pressure values are substantially constant as a function of time and the PWTT values decrease as a function of time.

It will further be appreciated that the presented method cannot only be applied to patients with congestive heart failure but to cardiovascular risk groups in general. Furthermore, the method could be applied to athletes, astronauts and the like in order to detect cardiovascular changes.

BRIEF DESCRIPTION WITH RESPECT TO THE FIGURES

Figure 2:
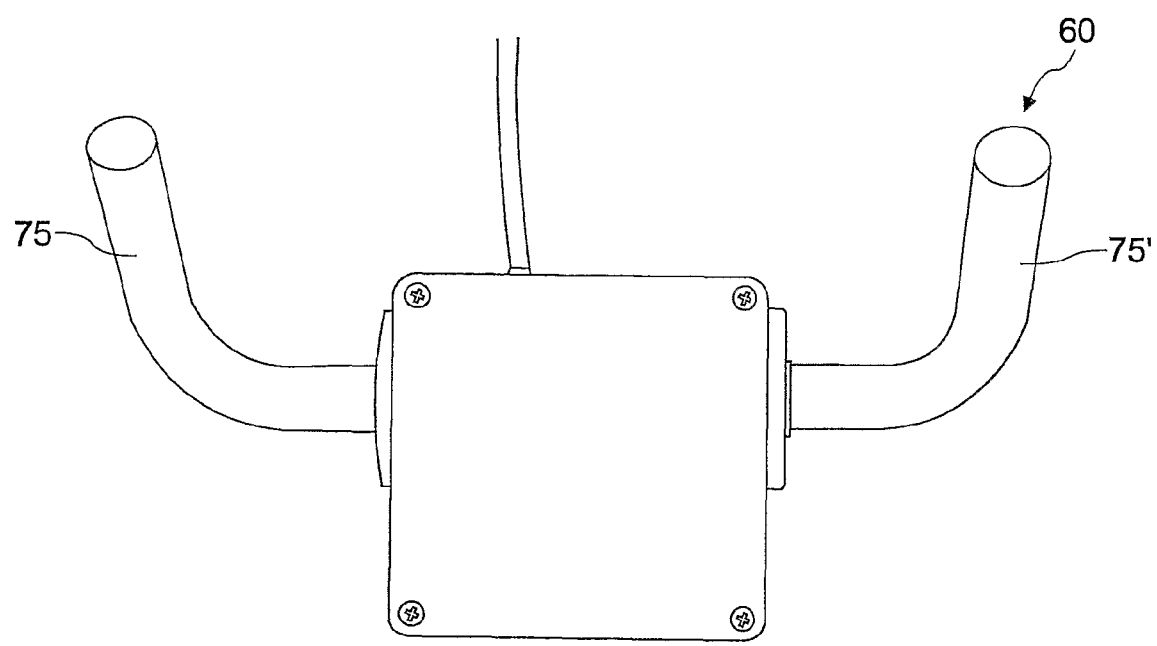
Figure 3:
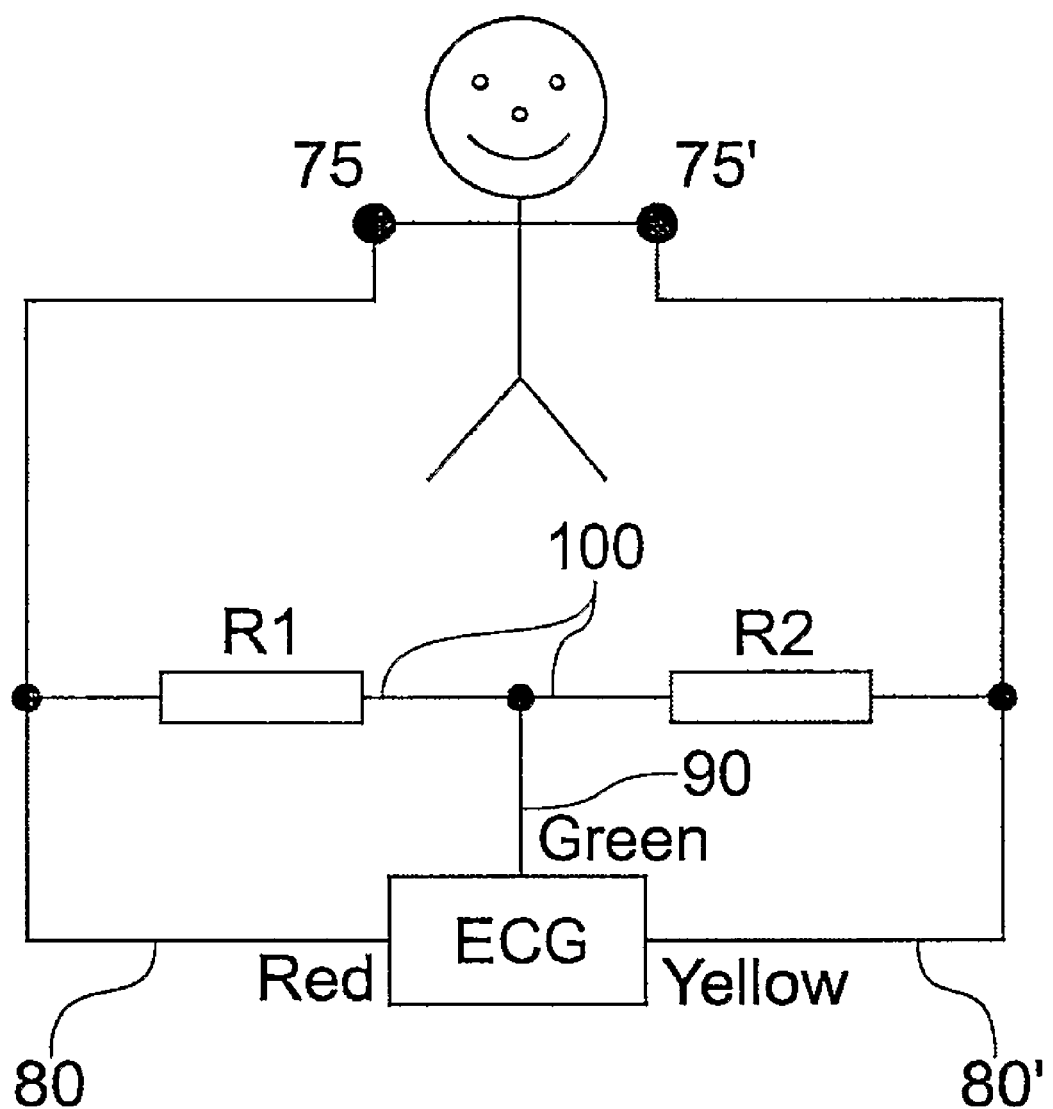
Figure 4:
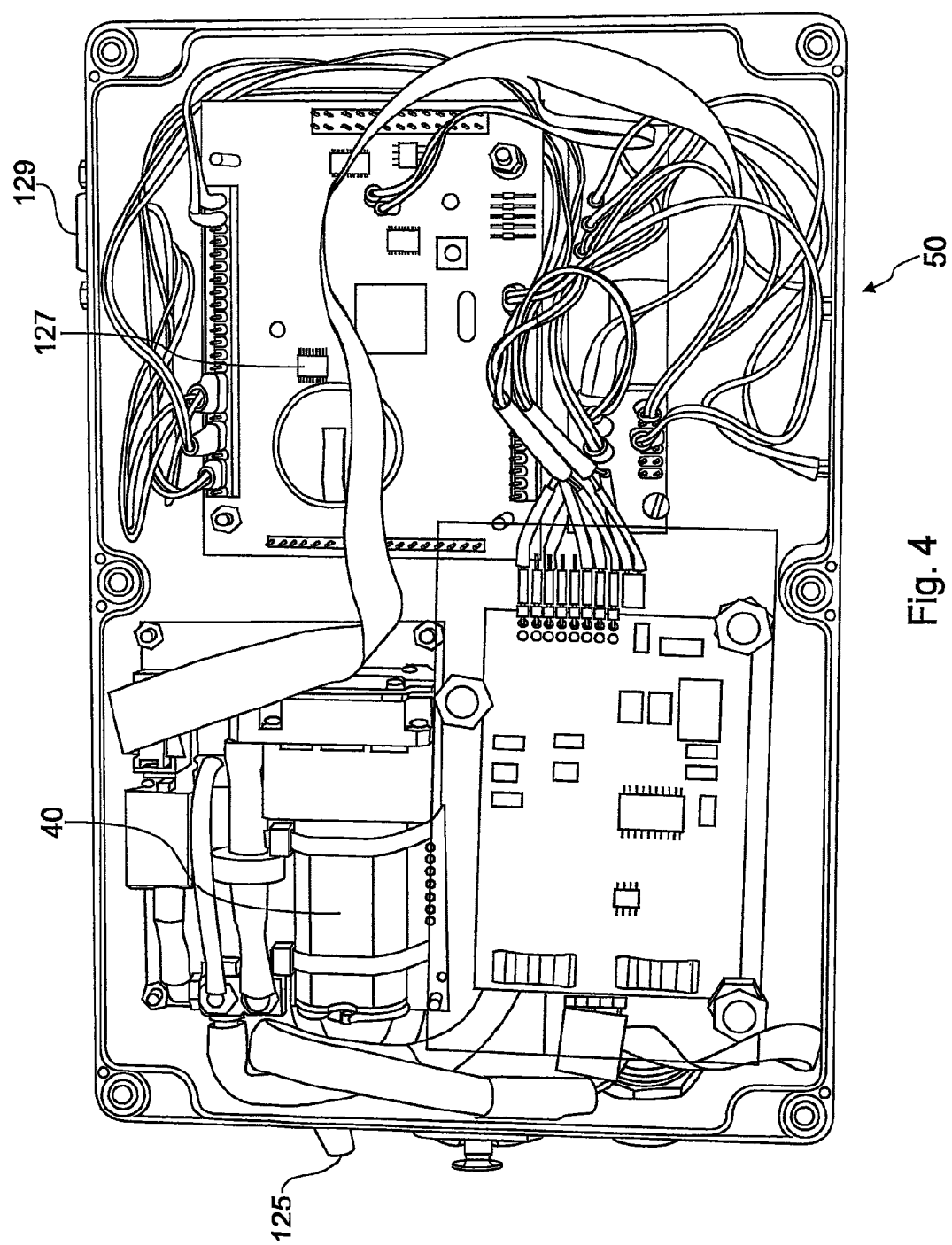
Figure 5:
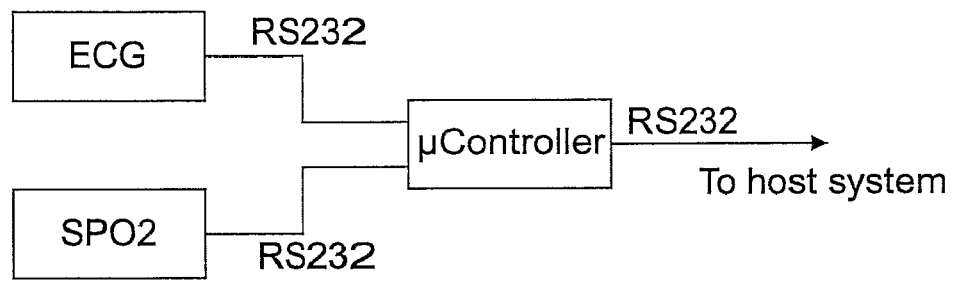
Figure 6:
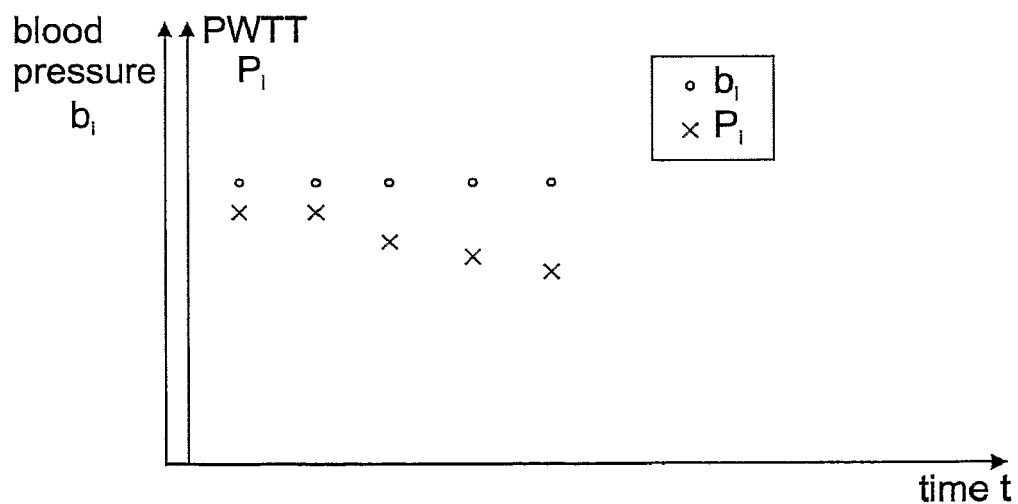
Figure 7:
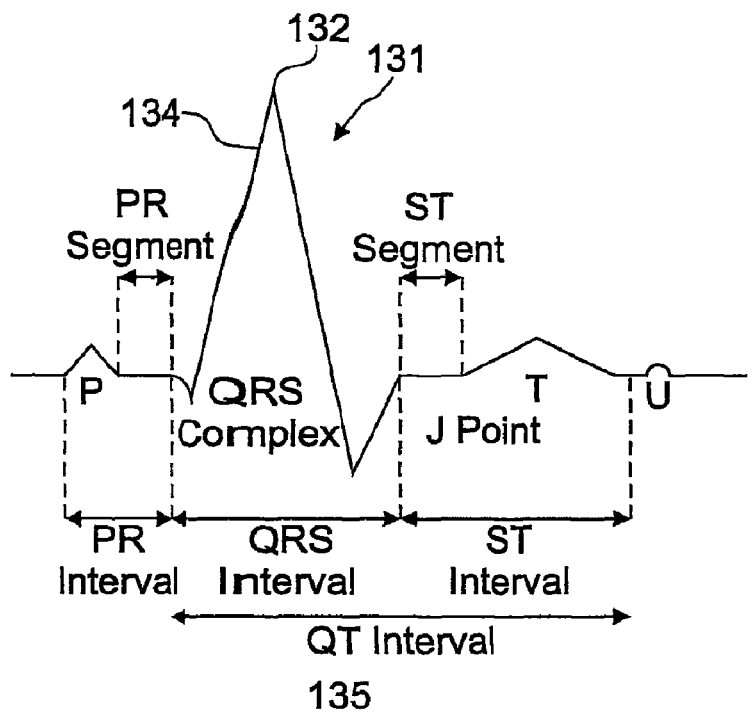
Figure 8:
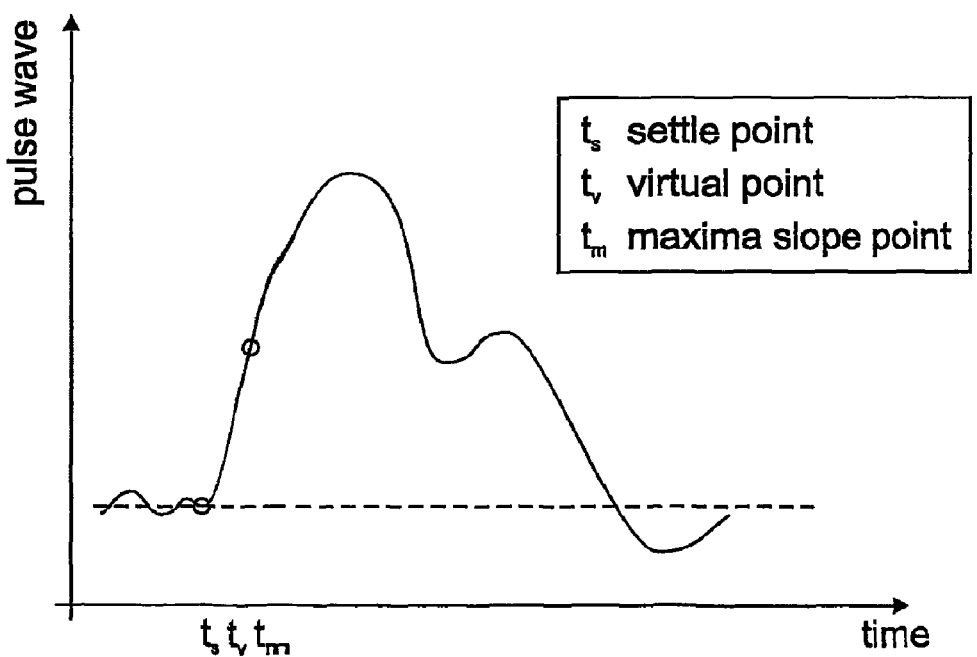

The present invention will be more apparent from the following description of a not limiting embodiment with reference to the attached drawings, wherein FIG. 1: is a schematic view of an apparatus for non-invasive heart monitoring according to the invention;

FIG. 2: is a schematic view of an electrocardiogram measuring device of the apparatus of FIG. 1;

FIG. 3: is an illustration of a connection scheme for the electrocardiogram measuring device presented in FIG. 2;

FIG. 4: is a detailed view of a process unit of the apparatus of FIG. 1;

FIG. 5: shows a microcontroller with its input-output data connections;

FIG. 6: is a graph showing a one-dimensional histogram with an abscissa axis indicative of a time evolution and two different ordinate axes, one indicative of the PWTT values $P_i$ and another indicative of the blood pressure values $b_i$;

FIG. 7: illustrates an electrocardiogram curve;

FIG. 8: is a graph illustrating the geometrical calculation of the virtual point $t_v$, which is used as a characteristic point of the SpO2 curve.

DETAILED DESCRIPTION

FIG. 1 shows a schematic view of an apparatus for non-invasive heart monitoring. The apparatus is used to monitor changes in heart dynamics of patients with congestive heart failure. The apparatus 10 generally comprises a pulse wave measuring device for measuring a pulse wave, a non-invasive blood pressure measuring device 40 for non-invasive measuring of the blood pressure and a process unit 50. The apparatus further comprises a heart rhythm measuring system, which includes an electrocardiogram measuring device 60 for measuring an electrocardiogram and a QRS-wave detecting device (not shown) for detecting a QRS-wave on an electrocardiogram measured by the electrocardiogram measuring device 60.

The measuring devices 40 and 60 are connected to the process unit 50, which processes measured outputs from the electrocardiogram measuring device 60, from the pulse wave measuring device and from the non-invasive blood pressure measuring device 40 and transmits the measured outputs to a host system (not shown).

In this embodiment, the host system comprises the QRS-wave detecting device whereas the process unit 50 comprises the electrocardiogram measuring device 60. The detected QRS-wave allows to derive the heart rhythm as will be described in more detail later on. Furthermore, the host system comprises a pulse wave transit time determining device (not shown) for determining a pulse wave transit time (PWTT) based on detected outputs from the QRS-wave detecting device and on measured outputs from the pulse wave measuring device. The host system further comprises a first storing means (not shown) for storing PWTT values resulting of the pulse wave transit time determining, a second storing means (not shown) for storing blood pressure values resulting of the blood pressure measuring and a cardiovascular dynamic change calculating device (not shown) for calculating a relative change of PWTT values determined by the PWTT determining device and blood pressure values measured by the blood pressure measuring device 40 as a function of time. The cardiovascular dynamic change calculating device is connected to an alarm emitting device (not shown), which emits an alarm if the blood pressure values are substantially constant as a function of time and the PWTT values decrease as a function of time. As the relative change of the PWTT values and the blood pressure values as a function of time is used, it is not necessary to have the absolute PWTT and blood pressure values.

FIG. 2 shows such an electrocardiogram measuring device 60 where instead of conventional electrodes two electro-conducting grips 75, 75' are used to allow the electrocardiogram measuring. The patient only touches two metal grips 75, 75' with his hands thus allowing an easy handling of the electrocardiogram measuring device 60.

FIG. 3 illustrates a connection scheme of the electrocardiogram measuring device 60. The two metal grips 75, 75' are connected to the two inputs 80 and 80' of the electrocardiogram measuring device 60. A third input 90 is connected using a voltage divider 100.

In this particular case, the pulse wave measuring device is a photoplethysmograph based on a SpO2 measuring device. The SpO2 measuring device could also be used for a measurement of the blood oxygen saturation by determining the percentage of oxihemoglobin in a given body part (e.g. finger tip). The SpO2 measuring device uses the red light absorption of hemoglobin to identify changes of blood filling at the measurement point, which allows the detection of e.g. the moment of highest blood filling. The pulse wave measuring device can be connected to a photoelectric pulse wave sensor 105 to be put on the fingertip of a patient for detecting the arrival of the pulse wave.

The non-invasive blood pressure measuring device 40 uses an oscillometric method for measuring a blood pressure. Therefore, a cuff 110 is put around the upper arm 120 of the patient. The non-invasive blood pressure measuring device 40 can measure systolic, diastolic and mean arterial blood pressures.

FIG. 4 shows in more detail the components of the process unit 50. The blood pressure measuring device 40 can be connected to the cuff 110 via a cuff-connector 125. The cuff 110 is further coupled with a pump (not shown), an exhaust valve (not shown) and a pressure sensor (not shown) by way of a pipe (not shown). A signal representative of a pressure sensed by the pressure sensor (not shown) is applied to a cuff-pressure detect and amplifier unit (not shown). The pressure signal is detected and amplified by the cuff-pressure detect and amplifier unit, and converted into a corresponding digital signal by an A/D converter (not shown).

As the electrocardiogram measuring device 60 and the pulse wave measuring device which is realized in form of a SpO2 measuring device, have no interface for defined time synchronization, it is preferable to create a common time base. After the measured outputs from the electrocardiogram measuring device 60 and the pulse wave measuring means have been digitalized, they are transmitted to a synchronization unit 127. The synchronization unit 127 is realized in form of a programmable microcontroller 127, whose input-output data connections are illustrated in FIG. 5.

The microcontroller 127 has real-time capabilities to add continuously timestamps to the measured outputs from both the electrocardiogram measuring device 60 and the pulse wave measuring device. A data transfer of the electrocardiogram measuring device 60 and the pulse wave measuring device to the programmable microcontroller 127 is realized via a RS232 protocol. The microcontroller 127 affects the incoming data with timestamps and transmits the data to the host system. The host system has in this embodiment only one serial port, and therefore the data is multiplexed before it is transmitted to the host system via a serial port 129. The process unit 50 further comprises a connector for the photoelectric pulse wave sensor 105 of the pulse wave measuring device.

In an alternative embodiment, the host system can be omitted, and the QRS-wave detecting device, pulse wave transit time determining device, the cardiovascular dynamic change calculating device and the alarm emitting device can be integrated in the process unit 50. In this way, the patient could monitor himself without being under continuous surveillance by a physician. Upon an alarm has been emitted by the alarm emitting device, the patient could request medical help on its own. Naturally, the alarm could also be sent via telecommunication to a distant person, e.g. a physician, in order to directly request medical help.

The invention further provides a method for non-invasive heart monitoring, preferably of patients with congestive heart failure. In a preferred embodiment of the current invention, the method comprises the steps described in the following.

First, at step S1 occurring at time t1 an electrocardiogram e1 is measured by the electrocardiogram measuring device 60, a pulse wave pw1 is measured by the pulse wave measuring device and transferred to a synchronization unit 127 in order to synchronize the measurements of e1 and pw1. Substantially at the same time t1, that is to say within 2-10 minutes, a blood pressure b1 is measured by the blood pressure measuring device 40, whereby step S2 is defined.

At step S3 the synchronized data e1 and pw1 are transmitted together with the blood pressure value b1 to the host system. The host system receives the measured values, checks their integrity and stores them.

At step S4 the QRS-wave detecting device detects a QRS-wave qrs1 on the electrocardiogram e1. The host system evaluates a PWTT P1 based on the detected QRS-wave qrs1 from the QRS-wave detecting device and the pulse wave pw1 measured by the pulse wave measuring device.

One therefore obtains a pair of measurement values denoted in the following by the two-dimensional vector (P1, b1).

Steps S1 and S4 are repeated n times such that there results a time-series of measurement values (P1, b1), . . . , (Pn, bn). The frequency of the measurements can be varied as a function of need. For patients with CHF, the measurement values should be recorded at least once a day, in critical cases 3-5 times a day, and should in addition be repeated on a regular day-to-day basis. In other words, the measurements are repeated at predefined intervals.

As illustrated in FIG. 6, the time-series of measurement values can be visualized in form of a one-dimensional histogram with an abscissa axis indicative of a time evolution and two different ordinate axes, one indicative of the PWTT values Pi and another indicative of the blood pressure values bi. In other words, the PWTT values Pi and the blood pressure values bi are brought into a time-dependent relationship by using an one-dimensional histogram with a common time axis.

At step S5, the measurement values are further analyzed in the way that the host system calculates a relative change of the PWTT-values and the blood pressure values as a function of time. The PWTT-values are influenced by the blood pressure values. The higher the blood pressure is, the lower the PWTT is, that is, the lower the blood pressure is, the higher the PWTT is. However, when the blood pressure stays substantially constant as a function of time and the PWTT decreases as a function of time, this is an indication that the condition of the CHF patient has degraded. In such a case, it is recommended that the patient sees his physician or is medically treated in a hospital.

In a preferred embodiment, the host system determines therefore an amount of change $\Delta b = b_n - b_i$ of the blood pressure values $b_n$ and $b_i$ measured at time $t_n$ and $t_i$, respectively, and an amount of change $\Delta P = P_n - P_i$ of PWTT-values $P_n$ and $P_i$ also measured at time $t_n$ and $t_i$, respectively. The resulting slope $\Delta P/\Delta t$ in the time interval $\Delta t = t_n - t_i$ is used to judge whether the patient is subject to cardiodynamical changes: if the slope $\Delta P/\Delta t$ is negative while the blood pressure stays substantially constant—i.e. $b_n$ does not differ more than 15% from $b_i$—then an alarm signal is emitted (step S6).

The presented method allows thus to keep CHF patients under a continuous surveillance. It is further to be noted that this method can be applied to monitor cardiovascular changes in general. The method can for instance be used for a therapeutic control of patients with a heart failure, for an improved rehabilitation of cardiovascular diseases and for optimizing individual training conditions in sports.

So far only the PWTT and the blood pressure values have been used to judge whether the patient is subject to cardiodynamical changes. It is straight-forward to include further physiological parameters in the monitoring method. Such physiological parameters can for instance be the weight of the patient, its blood sugar level, its heart rate variability, its breathing frequency, the oxygen saturation of the patient's blood and/or its pulmonary function.

In the following the details of the PWTT measurement are described. The PWTT is obtained by measuring the time interval from the moment the pulse wave is leaving the left ventricle of the heart to the moment when it arrives at the fingertip. The R-peak on the QRS-wave indicates the moment of the heart's maximum excitation, which indicates the moment of the highest left-ventricular pressure and thus defines a heart rhythm. At this heart rhythm, the pulse wave leaves the left ventricle to run through the vessels.

The electrocardiogram signal is based on a significant curve progressing, which is repeated from heartbeat to heartbeat. For the PWTT calculation, one characteristic point on the electrocardiogram curve 131 is searched for in order to have a unique reference point (FIG. 7). For this purpose the R-peak 132 of the electrocardiogram curve 131 is selected. The R-peak 132 indicates the starting point of the ventricular ejection. The signal has relative high amplitude and is preceded by a steep slope 134, which is part of the QRS-complex 135.

The mathematical R-peak detection can be split up in different parts. The first part consists of signal filtering and it is followed by signal derivation. The derived signal is statistically analyzed with a histogram and finally a post-processing algorithm defines the R-peak 132.

Signal filtering is used to reduce the effect of interfering signals. Muscle artifacts and signal noise for example generate such interfering signals. The interesting part of the characteristic electrocardiogram curve 131 has a frequency range from 0.5 Hz to 50 Hz. Therefore, first, a low pass filter with a cut off frequency of 50 Hz is used. After this a high pass filter with a cut off frequency of 0.5 Hz is used.

Like mentioned before, the R-peak is preceded by a significant positive slope. The significance is the maximum positive slope during a characteristic electrocardiogram curve period. The slope can be calculated with the derivation of the filtered signal. To amplify the maximum slope of the electrocardiogram signal, the derived signal is normalized and processed with the following function f(x) in order to damp lower slope values:

$$f(x)=\text{sig}(x) \cdot x^2.$$

The next step is the analysis of the slope distribution. A histogram analysis is used to define a possible maxima level. The maxima level is then used to locate points where the curve passes with a positive slope and defines timestamp markers. The located slope maxima are situated at the left side of the R-peak. An advantageous way to find the peak consists in following the positive slope of the electrocardiogram signal with a Boolean "greater as" operation. The starting points are defined by the timestamps of the slope maxima.

In order to calculate a representative PWTT-value the measured outputs from the pulse wave measuring device have to be evaluated in a similar way to the electrocardiogram curve mentioned above. The measured outputs are for instance available under the form of a SpO2 curve measured by the SpO2 measuring device.

Due to the nature of the SpO2 curve and the measurement method, the signal is influenced by wave reflections. The significant point of the SpO2 curve is preferentially measured at the leading slope of the systolic pulse wave. This part of the wave is the least influenced by wave reflections. Furthermore, it is preferable to set up a virtual characteristic point with the information of two significant curve points of the SpO2 signal, to get a more robust and precise calculation method (Peter Elter: *Methoden und System zur nichtinvasiven, kontinuierlichen und belastungsfreien Blutdruckmessung*, Institut für Technik und Informationsverarbeitung, Universität Karlsruhe). The two points are defined by the lower settle point ($t_s$) of the leading systolic pulse wave and its maximum slope ($t_m$). These two points are defining the virtual point $t_v$, used as characteristic point of the SpO2 curve. The geometrical calculation of this virtual point is shown in FIG. 8. The characteristic point $t_v$ can of course be replaced by any other accurately determinable point on the SpO2 curve.

| Reference numerals | |
| --- | --- |
| apparatus | 10 |
| pulse wave measuring device | 30 |
| blood pressure measuring device | 40 |
| process unit | 50 |
| electrocardiogram measuring device | 60 |
| electro-conducting grips | 75, 75' |
| two inputs | 80, 80' |
| third input | 90 |
| voltage divider | 100 |
| pulse wave sensor | 105 |
| cuff | 110 |
| upper arm | 120 |
| cuff-connector | 125 |
| synchronization unit | 127 |
| serial port | 129 |
| electrocardiogram curve | 131 |
| R-peak | 132 |
| steep slope | 134 |
| QRS-complex | 135 |

The invention claimed is:

1. An apparatus for non-invasive heart monitoring comprising:
   (a) a pulse wave transit time (PWTT) determining device for determining a PWTT at predefined intervals;
   (b) a first storing means for storing resulting PWTT values;
   (c) a blood pressure measuring device for measuring a blood pressure close in time with said determining; and
   (d) a second storing means for storing resulting blood pressure values,
   wherein, said apparatus further comprises:
   (e) a cardiovascular dynamic change calculating device for calculating a relative change of said PWTT values and said blood pressure values as a function of time; and
   (f) an alarm emitting device for emitting an alarm when said blood pressure values are substantially constant as a function of time and said PWTT values decrease as a function of time.

2. The apparatus according to claim 1, wherein the apparatus is connected to a host system for remotely monitoring said relative change.

3. The apparatus according to claim 1, further comprising a human weight measuring device for measuring a human weight, a breathing frequency measuring device for measuring a breathing frequency, a heart rate variability measuring device for measuring a heart rate variability, a blood sugar level measuring device for measuring a blood sugar level, a blood oxygen saturation measuring device for measuring a blood oxygen saturation and/or a pulmonary function measuring device for measuring a pulmonary function.

4. The apparatus according to claim 1, wherein said pulse wave transit time determining device comprises a heart rhythm measuring system and a pulse wave measuring device.

5. The apparatus according to claim 4, wherein said heart rhythm measuring system comprises: (a) an electrocardiogram measuring device and a QRS-wave detecting device, (b) an impedance plethysmograph or (c) a phonocardiograph.

6. The apparatus according to claim 4, wherein said pulse wave measuring device is a photoplethysmograph based on a SpO2 measuring device.

7. A method for non-invasive heart monitoring comprising the steps of:
   (a) determining a pulse wave transit time (PWTT) at predefined intervals;
   (b) storing PWTT values resulting from said determining;
   (c) measuring a blood pressure close in time with said determining of said PWTT; and
   (d) storing blood pressure values resulting from said measuring,
   wherein, the method further comprises the steps of:
   (e) calculating a relative change of said PWTT values and said blood pressure values as a function of time; and
   (f) emitting an alarm when said blood pressure values are substantially constant as a function of time and said PWTT values decrease as a function of time.

8. The method according to claim 7, wherein human weight is included as additional physiological observation parameter.

9. The method according to claim 7, wherein breathing frequency is included as additional physiological observation parameter.

10. The method according to claim 7, wherein heart rate variability is included as additional physiological observation parameter.

11. The method according to claim 7, wherein blood sugar level is included as additional physiological observation parameter.

12. The method according to claim 7, wherein blood oxygen saturation is included as additional physiological observation parameter.

13. The method according to claim 7, wherein pulmonary function is included as additional physiological observation parameter.

14. The method according to claim 7, further comprising the step of applying said method to patients with congestive heart failure.

15. The method according to claim 7, further comprising the step of applying said method to athletes and/or astronauts.

16. The method according to claim 7, wherein said PWTT is derived by means of a heart rhythm measuring system and a pulse wave measuring device.

17. The method according to claim 16, wherein said heart rhythm measuring system comprises: (a) an electrocardiogram measuring device and a QRS-wave detecting device, (b) an impedance plethysmograph or (c) a phonocardiograph.

* * * * *